(12) United States Patent
Benchikh et al.

(10) Patent No.: US 8,476,029 B2
(45) Date of Patent: Jul. 2, 2013

(54) MCPP IMMUNOASSAY

(76) Inventors: Elouard Benchikh, Antrim (GB);
Stephen Peter Fitzgerald, Antrim (GB);
Paul John Innocenzi, Antrim (GB);
Philip Andrew Lowry, Antrim (GB);
Ivan Robert McConnell, Antrim (GB)

( * ) Notice: Subject to any disclaimer, the term of this patent is extended or adjusted under 35 U.S.C. 154(b) by 39 days.

(21) Appl. No.: 13/377,522

(22) PCT Filed: May 26, 2010

(86) PCT No.: PCT/GB2010/050874
§ 371 (c)(1),
(2), (4) Date: Dec. 28, 2011

(87) PCT Pub. No.: WO2010/142974
PCT Pub. Date: Dec. 16, 2010

(65) Prior Publication Data
US 2012/0135434 A1    May 31, 2012

(30) Foreign Application Priority Data
Jun. 11, 2009   (GB) .................................. 0910031.4

(51) Int. Cl.
*G01N 33/53*    (2006.01)

(52) U.S. Cl.
USPC .......................................... 435/7.1; 436/518

(58) Field of Classification Search
None
See application file for complete search history.

(56) References Cited

PUBLICATIONS

Staack, R.F., et al., "Proof of a 1-(3-chlorophenyl)piperazine (mCPP) intake—Use as adulterant of cocaine resulting in drug-drug interactions?" Journal of Chromatography B, 855: 127-133, 2007.
Mayol, R.F., et al., "Characterization of the Metabolites of the Antidepressant Drug Nefazodone in Human Urine and Plasma." Drug Metabolism and Disposition, 22: 304-311, 1994.
Bowles, M., et al., "Large Scale Production and Purification of Paraquat and Desipramine Monoclonal Antibodies and their FAB Fragments." International Journal of Immunopharmacology, 10: 537-545, 1988.
Goeringer, K.E., et al., "Postmortem Forensic Toxicology of Trazodone." Journal of Forensic Sciences, 45:2000-2007, 2000.
King, L.A., "m-chlorophenylpiperazine (mCPP)." Internet Citation, Jan. 1, 2007, pp. 1-15.
Lamont, J.V., et al., "Development of antibodies for the measurement of trazodone and related compounds." Clinical Chemistry, American Association for Clinical Chemistry, Washington, D.C., 55(6): A251, Suppl, 2009.

*Primary Examiner* — Jacob Cheu
(74) *Attorney, Agent, or Firm* — Zackson Law LLC; Saul L. Zackson

(57) ABSTRACT

The invention describes a practical and robust multi-antibody approach to the sensitive immunodetection and determination of the drug of abuse m-chlorophenyl piperazine (mCPP). The invention also describes methods and kits for mCPP detection in an in vitro sample.

16 Claims, 2 Drawing Sheets

Trazodone  mCPP

MCPP IMMUNOASSAY

CROSS REFERENCE TO RELATED APPLICATIONS

This application claims benefit of priority from PCT application PCT/GB2010/050,874 filed May 26, 2010, and from GB Patent Application No. 0910031.4 filed Jun. 11, 2009. Each of these applications is incorporated herein by reference in its entirety.

FIELD OF THE INVENTION

The invention relates to a novel, practical and robust method for the unequivocal identification of the drug of abuse mCPP.

BACKGROUND TO THE INVENTION 1-(3-chlorophenyl)piperazine, common name m-chlorophenylpiperazine (mCPP), is the main metabolite of the widely used antidepressant drug, trazodone, and its less commonly-used analogue nefazodone. It is a serotonin receptor agonist that affects hormone levels, physiology and behaviour, and is known to be a mild hallucinogen with weak ecstasy-like effects. A report by the European Union-funded European Monitoring Centre for Drugs and Drug Addiction (EMCDDA) and Europol describes its increasing abuse across Europe and it is described as the most widely encountered new psychoactive substance since the inception of a European drug monitoring early warning system in 1997 (Europol-EMCDDA Active Monitoring Report on a new psychoactive substance). It is scheduled in several European countries as well as New Zealand, the apparent origin of its use as a "party pill".

An impediment to testing for mCPP intake is the metabolic production of mCPP by the antidepressant drugs trazodone and nefazodone. Trazodone, systematic name 2-(3-[4-(3-chlorophenyl)piperazin-1-yl]propyl)-[1,2,4]triazolo[4,3-α]pyridin-3(2H)-one, is an antidepressant drug with anxiolytic and hypnotic activity which is metabolized in the liver by hydroxylation, dealkylation and N-oxidation. Staack et al (2007) developed a technique to overcome the possibility of a false-positive test for mCPP intake using gas chromatography and mass spectroscopy (GC-MS). The test rules out trazodone intake by detecting either the parent molecule trazodone or the metabolite hydroxytrazodone. Nefazodone is eliminated as a possible mCPP source by detection of the major metabolites hydroxyl nefazodone and hydroxyethyl deamino hydroxyl nefazodone, both found at higher levels than mCPP. It is reported that mCPP is a minor urinary metabolite of nefazodone in humans, representing less than 1% of total metabolites (Mayol et al. 1994). The drawbacks of the Staack test for mCPP intake are the protracted pre-treatment steps required to prepare derivatives that are amenable to gas chromatography, the expensive and highly-specialised equipment required which is unsuitable and impractical for application outside of the laboratory, and the requirement of an external reference standard of trazodone to confirm the retention time to support an accurate examination of the GC-MS spectra. Furthermore, the requirement of 'careful screening' to differentiate between mCPP intake and trazodone implies a method that is non-robust.

Specific binding reactions, such as antibody-antigen interactions, have been used extensively in immunoassays to detect a variety of substances present in tissue extracts. Thus, for example, radioimmunoassays (RIAs) could be used for the determination of mCPP and drugs that produce mCPP as a metabolic product. Radioimmunoassays are very sensitive, but do require radionuclide tracers, for example $^{125}I$ and $^{3}H$. There are no known RIAs for mCPP and drugs that produce mCPP as a metabolic product such as trazodone. Enzyme-linked immunosorbent assays (ELISAs) are a non-radioactive alternative that could be used for the qualitative and quantitative determination of mCPP and drugs that produce mCPP as a metabolic product.

To enable drug screening of mCPP for clinical and forensic toxicology purposes, an economically viable, practical, sensitive and robust test is required. The invention described herein, based on the antibody-antigen interaction, possesses these attributes.

SUMMARY OF THE INVENTION

The invention provides a solution to the problem of the unequivocal and practical analytical detection and determination of mCPP intake. This solution requires the use of antibodies that bind to mCPP together with antibodies specific for drugs that produce mCPP as a metabolic product.

A first aspect of the invention is an antibody or antibodies specific for a drug or drugs that produce mCPP as a metabolic product together with an antibody that binds mCPP for use in an in vitro test for mCPP intake. The drug that produces mCPP as a metabolic product is preferably trazodone or nefazodone. The drugs that produce mCPP as a metabolic product are preferably trazodone and nefazodone.

In a second aspect, the present invention describes a method of detecting or determining mCPP intake in an individual. The method comprises contacting an in vitro sample taken from the individual with two or more conjugates and one or more antibodies specific for a drug that produces mCPP as a metabolic product and at least one antibody that binds an epitope of mCPP. The bound conjugates are detected and the presence of or amount of non-metabolic mCPP deduced using calibration values. The drug that produces mCPP as a metabolic product is preferably trazodone or nefazodone. The drugs that produce mCPP as metabolic products are preferably trazodone and nefazodone. For example, an assay to distinguish between trazodone and mCPP intake would incorporate a trazodone-specific antibody, an antibody sensitive to mCPP and appropriate conjugates for their detection and quantification. An assay to distinguish between trazodone, nefazodone and mCPP intake could incorporate a trazodone-specific antibody, a nefazodone-specific antibody and an antibody sensitive to mCPP and appropriate conjugates for their detection and quantification. The meaning of specific herein is as would be interpreted by the skilled person in the art of immunoassays, in which the binding of non-target analytes by an analyte-specific antibody used in an assay is at a low or non-measurable level so as not to compromise the validity of the assay. The sample can be any peripheral biological fluid but is preferably urine. In the context of the invention reference to a sample implies one or more samples. The conjugates of the method are made up of haptens attached to labelling agents. The haptens of the conjugates are molecules that can bind to the antibodies of the method. The use of haptens, conjugates and antibodies in the context of immunoassays is well known in the art. Preferably, the labelling agent of the conjugates is selected from an enzyme, a luminescent substance, a radioactive substance, or a mixture thereof. More preferably, the labelling agent is an enzyme, preferably a peroxidase, most preferably horseradish peroxidase (HRP).

Alternatively, or additionally, the luminescent substance may be a bioluminescent, chemiluminescent or fluorescent material.

A further aspect of the invention is a kit for detecting or determining mCPP intake, the kit including one or more antibodies specific for a drug or drugs that produce mCPP as a metabolic product and an antibody that binds mCPP. Another embodiment of the invention is a kit for detecting or determining mCPP intake that includes one or more antibodies specific for a drug or drugs that produce mCPP as a metabolic product and an antibody that binds an epitope of mCPP. The drug that produces mCPP as a metabolic product is preferably trazodone or nefazodone. Alternatively, the drugs that produce mCPP as a metabolic product are trazodone and nefazodone. The kit may optionally include instructions for the use of said conjugates and said antibodies for detecting or determining mCPP and drugs that produce mCPP as a metabolic product.

DETAILED DESCRIPTION OF THE INVENTION

Methods, Examples and Results

Preparation of Haptens, Immunogens and Conjugates

Figure 1:
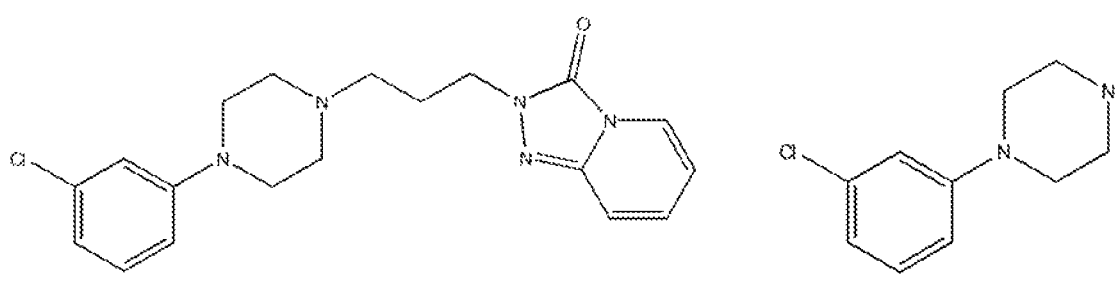
FIG. 1 Structures of trazodone and mCPP

Although haptens provide defined structural epitopes, they are not in themselves immunogenic and therefore need to be conjugated to carrier materials, which will elicit an immunogenic response when administered to a host animal. Appropriate carrier materials commonly contain poly(amino acid) segments and include polypeptides, proteins and glycoproteins. Illustrative examples of useful carrier materials are bovine serum albumin (BSA), egg ovalbumin, bovine gamma globulin, bovine thyroglobulin (BTG), keyhole limpet haemocyanin (KLH) etc. Alternatively, synthetic poly(amino acids) having a sufficient number of available amino groups, such as lysine, may be employed, as may other synthetic or natural polymeric materials bearing reactive functional groups. In particular, carbohydrates, yeasts or polysaccharides may be conjugated to the hapten to produce an immunogen. The haptens can also be coupled to a detectable labelling agent such as an enzyme (for example, horseradish peroxidase), a substance having fluorescent properties or a radioactive label for the preparation of conjugates (or detection reagents) for use in the immunoassays. The fluorescent substance may be, for example, a monovalent residue of fluorescein or a derivative thereof. Immunogen formation involves conventional conjugation chemistry in which the oxygen of the hydroxyl group of Hapten A (FIG. 2) combines first with DCC and then NHS to form an ester with a powerful leaving group. Nucleophilic attack on the carbonyl of the ester functionality by a amine group on the protein (BSA or BTG), results in an amide bond and formation of the target immunogen. In order to confirm that adequate conjugation of hapten to carrier material has been achieved, prior to immunisation, each immunogen is evaluated using matrix-assisted UV laser desorption/ionisation time-of-flight mass spectroscopy (MALDI-TOF MS).

General Procedure for MALDI-TOF Analysis of Immunogens.

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 µl) were analysed using a matrix of Sinapinic acid and bovine serum albumin (Fluka) was used as an external calibrant.

Preparation of Antisera

In order to generate polyclonal antisera, the immunogen of the present invention is mixed with Freund's Adjuvant and the mixture is injected into a host animal, such as rabbit, sheep, mouse, guinea pig or horse. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilised on a solid support, purification steps can be taken to remove undesired material and eliminate non-specific binding.

Immunoassay Development

The process of developing an immunoassay is well known to the person skilled in the art. Briefly, for a competitive immunoassay in which the target analyte is a non-immunogenic molecule commonly referred to as a hapten, the following process is conducted: antibodies are produced by immunising an animal, preferably a mammalian animal, by repeated administration of an immunogen. The serum from the immunised animal is collected when the antibody titre is sufficiently high. A conjugate is added to a sample containing the target analyte and the raised antibodies, and the conjugate and analyte compete for binding to the antibodies. The process may comprise fixing said serum antibodies to a backing substrate such as a polystyrene solid support or a biochip. The antibodies can be polyclonal or monoclonal. The signal emitted in the immunoassay is proportionate to the amount of conjugate bound to the antibodies which in turn is inversely proportionate to the analyte concentration. The signal can be detected or quantified by comparison with a calibrator.

Example 1

Figure 2:
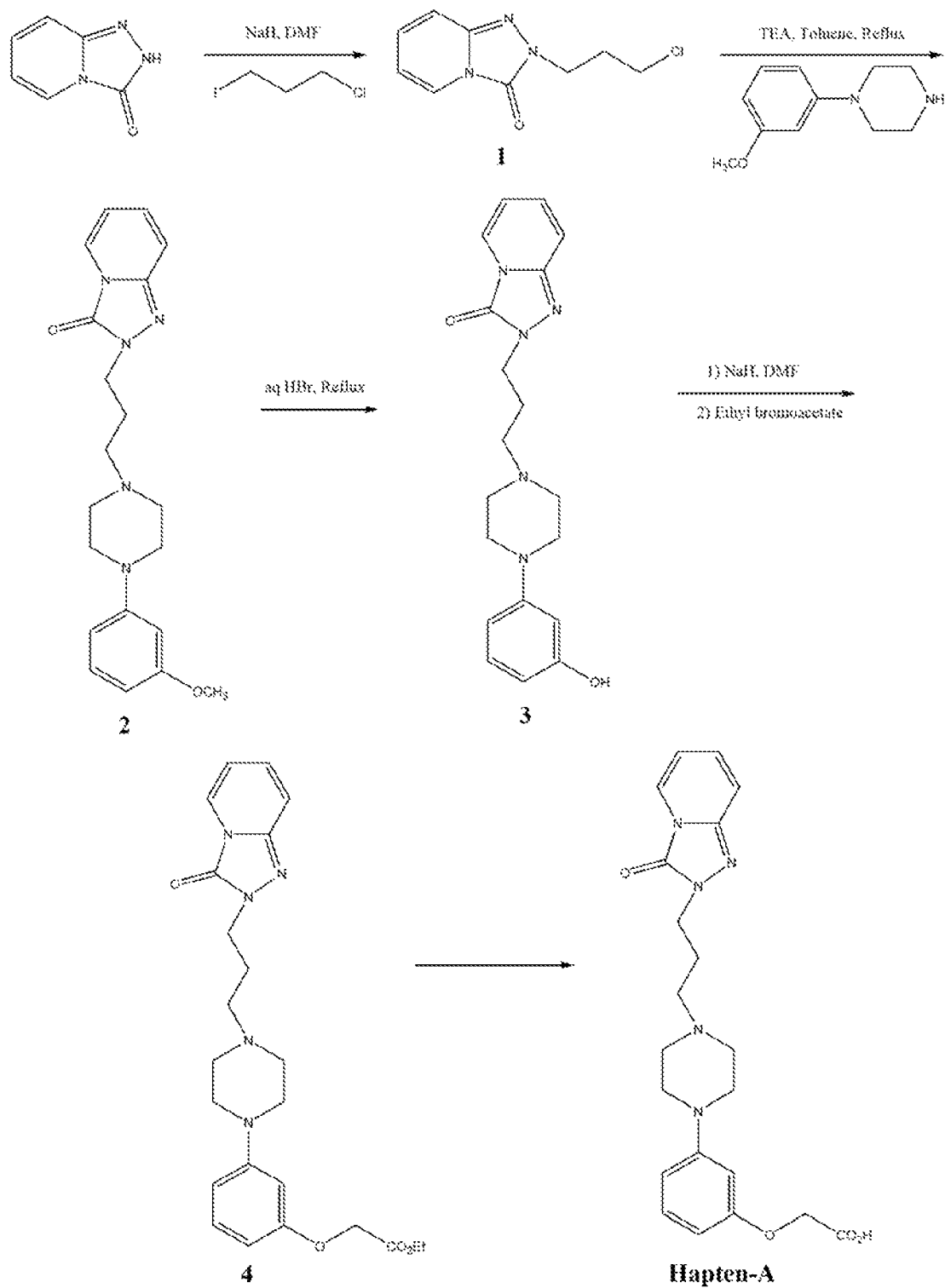
FIG. 2 Synthesis of hapten A

Preparation of 2-(γ-chloropropyl)-1,2,4-triazolo[4,3-a]pyridin-3(2H)-one (Structure 1, FIG. 2)

To a preheated solution at 80° C. of 1,2,4-triazolo[4,3-a]pyridin-3(2H)-one (25 g, 0.18 mol) in DMF (200 ml) under nitrogen was added sodium hydride (60%) (7.37 g). The mixture was heated at 80° C. for 1 hour under stirring, then 1-chloro-3-iodopropane (37.26 g, 0.18 mol) was added. The mixture was heated under stirring at 100° C. for 6 hours, and left at room temperature overnight. The solid formed was filtered off, washed by DMF (10 ml) and the filtrate was concentrated to dryness. The crude product obtained was diluted with saturated NaHCO$_3$ (300 ml) and the solution extracted with ethyl acetate (2×300 ml). The combined organic layers were washed by water (200 ml), brine (200 ml), dried over Na$_2$SO$_4$, filtered and concentrated to dryness to give the title compound 1 (20.1 g) as a viscous oil.

Example 2

Preparation of 3-methoxytrazodone (Structure 2, FIG. 2)

To a solution of the compound 1 (12 g, 0.057 mol) in anhydrous toluene (200 ml) was added 1-(3-methoxyphenyl)

piperazine hydrochloride (13.0 g, 0.057 mol) and triethylamine (TEA) (15.9 ml, 0.114 mol). The resulting mixture was heated at reflux for 6 hours. The solution was cooled at room temperature, washed with water (150 ml), brine (100 ml), dried over $Na_2SO4$, filtered and the solvent removed under reduced pressure. The residue obtained was purified by column chromatography (5% methanol/95% chloroform) to give 3-methoxytrazodone (10.6 g) as a white solid. $^{13}C$ NMR (δ: ppm): 162.44, 154.44, 150.63, 143.63, 132.24, 131.11, 124.96, 116.52, 112.98, 110.52, 106.51, 104.09, 57.24, 55.95, 54.69, 50.64, 45.95, 27.03.

Example 3

Preparation of 3-hydroxytrazodone (Structure 3, FIG. 2)

To a solution of hydrobromic acid 48 wt % in water (200 ml) was added 3-methoxytrazodone (9.5 g, 0.026 mol) and the mixture was heated at reflux for 3 hours. The solution was cooled to room temperature and concentrated to dryness. Water was then added (200 ml), neutralized to pH 7-8 and the solution extracted with ethyl acetate (3×150 ml). The combined organic layers were washed by water (150 ml), brine (150 ml), dried over $Na_2SO4$, filtered and concentrated to dryness. The crude product was recrystallized from ethyl acetate/hexane to give 3-hydroxytrazodone (6.5 g) as a white solid.

Example 4

Preparation of 3-(ethoxycarbonylmethoxy)trazodone (Structure 4, FIG. 2)

To a suspension of sodium hydride (NaH) (685 mg, 0.02 mol) in DMF (50 ml) under nitrogen was added a solution of 3-hydroxytrazodone (6.0 g, 0.017 mol) in DMF (100 ml) over a period of 15 minutes and the mixture heated at 60° C. for 1 hour. After cooling the mixture to room temperature a solution of ethyl bromoacetate (3.4 g, 0.02 mol) in DMF (50 ml) was added to the mixture. The mixture was then heated again at 60° C. for 1 hour and stirred at room temperature overnight. The solution was concentrated to dryness, water (200 ml) was added and the pH of the solution was adjusted to 10 by NaOH (1N). The aqueous solution was then extracted with ethyl acetate (2×200 ml), washed with water (100 ml), brine (100 ml), dried over $Na_2SO4$, filtered and concentrated to dryness. The crude product was purified by chromatography on silica gel using chloroform/methanol (9/1) to give 3-(ethoxycarbonylmethoxy)trazodone (5.06 g) as a white solid. $^{13}C$ NMR (δ: ppm): 168.06, 157.82, 151.7, 147.63, 140.43, 128.74, 122.72, 114.37, 109.46, 108.71, 103.44, 102.29, 64.49, 60.29, 54.60, 52.06, 47.81, 43.44, 29.91, 29.02, 13.17.

Example 5

Preparation of 3-(carboxymethoxy)trazodone (Hapten A, FIG. 2)

3-(Ethoxycarbonylmethoxy)trazodone (4.5 g, 0.0102 mol) was dissolved in THF (100 ml) and water (100 ml). Potassium hydroxide (4.37 g, 0.032 mol) was added and the mixture was stirred overnight at room temperature. The THF was removed under reduced pressure and the aqueous solution acidified to pH 2 by HCl (2N). The resultant white solid was filtered, washed with water and dried. Recrystallization with methanol gave 3-(carboxymethoxy) trazodone (3.9 g) as a white solid. $^{13}C$ NMR (δ: ppm): 171.14, 161.46, 156.24, 150.65, 143.66, 132.27, 131.03, 124.97, 116.54, 112.98, 110.62, 107.51, 105.01, 68.89, 57.12, 54.51, 50.39, 45.84, 26.83.

Example 6

Conjugation of Hapten A to Bovine Serum Albumin (BSA)

To a solution of Hapten A (30.8 mg, 0.075 mM) in pyridine (2.5 ml) was added N,N-dicyclohexylcarbodiimide (DCC) (15.5 mg, 0.075 mM) and N-hydroxysuccinimide (8.63 mg, 0.075 mM) and the mixture was stirred at room temperature overnight. The dicyclohexylurea formed was removed by filtration and the solution was added drop-wise to a solution of BSA (100 mg, 1.5 µmol) in 50 mM sodium bicarbonate solution (5 ml). The mixture was stirred overnight at 4° C. The solution was dialysed with 50 mM phosphate buffer pH 7.2 (3 changes) for 24 hours at 4° C., and freeze-dried. MALDI results showed 14.77 molecules of hapten A had been conjugated to one molecule of BSA.

Example 7

Conjugation of Hapten A to BTG

To a solution of Hapten A (55.54 mg, 0.1325 mM) in pyridine (2.5 ml) was added N,N-dicyclohexylcarbodiimide (DCC) (55.62 mg, 0.27 mM) and N-hydroxysuccinimide (31.07 mg, 0.27 mM) and the mixture was stirred at room temperature overnight. The dicyclohexylurea formed was removed by filtration and the solution was added dropwise to a solution of BTG (150 mg, 2.25 µmol) in 50 mM sodium bicarbonate solution (10 ml). The mixture was then stirred overnight at 4° C. The solution was then dialysed with 50 mM phosphate buffer pH 7.2 (3 changes) for 24 hours at 4° C., and freeze-dried.

Example 8

Conjugation of Hapten A to HRP

EDC hydrochloride (10 mg) was dissolved in water (0.5 ml) and immediately added to a solution of Hapten A (2 mg) in DMF (0.2 ml). After mixing, the solution was added drop-wise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The hapten-HRP conjugate was then dialysed overnight with 10 L of PBS at pH 7.2 at 4° C.

Example 9

Preparation of Ethyl 6-[N'-(3-chlorophenyl)-N-piperazinyl]hexanoate

To a solution of 1-(3-chlorophenyl)piperazine hydrochloride (12 g, 0.051 mol) in anhydrous toluene (250 ml) was added triethylamine (TEA) (15.6 ml, 0.112 mol) and ethyl 6-bromohexanoate (13.6 g, 0.061 mol) and the mixture heated at reflux for 4 hours. The mixture was then cooled to room temperature, washed with water (2×100 ml), brine (100 ml), dried over $Na_2SO4$, filtered and concentrated to dryness.

The residue obtained was purified by flash chromatography on silica gel using ethyl acetate/hexane (1/1) to give ethyl 6-[N'-(3-chlorophenyl)-N-piperazinyl]hexanoate (10.3 g) as a clear oil.

Example 10

Preparation of 6-[N'(3-chlorophenyl)-N-piperazinyl]hexanoic Acid

To a solution of [N-(carboethoxypentyl)-N-(3-chlorophenyl)]piperazine 5 (10 g, 0.029 mol) in a mixture of THF/water (1/1) was added potassium hydroxide (12 g, 0.087 mol) and the mixture was stirred at room temperature overnight. The THF was removed under vacuum and the solution was acidified with HCl (2N). The precipitate was filtered, washed by water and dried. Recrystallization with methanol gave 6-[N'-(3-chlorophenyl)-N-piperazinyl]hexanoic acid (6.5 g). $^{13}$C NMR (δ: ppm): 177.61, 152.78, 136.6, 132.15, 122.18, 118.15, 116.29, 58.21, 53.3, 47.86, 34.83, 27.43, 25.77, 25.18.

Example 11

Conjugation of 6-[N'-(3-chlorophenyl)-N-piperazinyl]hexanoic Acid to BSA

To a cooled solution at 0° C. of 6-[N'-(3-chlorophenyl)-N-piperazinyl]hexanoic acid (37.28 mg, 0.12 mmol) in DMF (3 ml) under nitrogen was added tri-n-butylamine (31.42 µl, 0.132 mmol) and isobutyl chloroformate (IBCF) (17.02 µl, 0.132 mmol). The mixture was stirred at 0° C. for 15 minutes and then added drop-wise to a cooled solution of BSA (100 mg) in sodium bicarbonate (100 mM, 10 ml) and the mixture was stirred at 4° C. overnight. The solution was then dialysed against 50 mM phosphate buffer pH 7.2 (3 changes) for 24 hours at 4° C., and freeze-dried. MALDI results showed 22.02 molecules of 6-[N'-(3-chlorophenyl)-N-piperazinyl] hexanoic acid had been conjugated to one molecule of BSA.

Example 12

Conjugation of 6-[N'-(3-chlorophenyl)-N-piperazinyl]hexanoic Acid to BTG

To a cooled solution at 0° C. of 6-[N'-(3-chlorophenyl)-N-piperazinyl]hexanoic acid (65.09 mg, 0.203 mmol) in DMF (3 ml) under nitrogen was added tri-n-butylamine (53.1 µl, 0.223 mmol) and isobutyl chloroformate (IBCF) (28.78 µl, 0.223 mmol). The mixture was stirred at 0° C. for 15 minutes and then added drop-wise to a cooled solution of BTG (150 mg) in sodium bicarbonate (100 mM, 10 ml) and the mixture was stirred at 4° C. overnight. The solution was then dialysed with 50 mM phosphate buffer pH 7.2 (3 changes) for 24 hours at 4° C., and freeze-dried.

Example 13

Conjugation of 6-[N'-(3-chlorophenyl)-N-piperazinyl]hexanoic Acid to HRP

To a cooled solution at 0° C. of 6-[N'-(3-chlorophenyl)-N-piperazinyl]hexanoic acid (2 mg) in DMF (200 µl) under nitrogen was added tri-n-butylamine (38 µl) and isobutyl chloroformate (IBCF) (2 µl). The mixture was stirred at 0° C. for 10 minutes and then added drop-wise to a cooled solution of HRP (200 mg) in water (800 µl) and the reaction mixture was incubated in the dark at room temperature overnight. Excess hapten was removed with double PD-10 columns (Pharmacia) in series, pre-equilibrated with PBS at pH 7.2. The hapten-HRP conjugate was then dialysed overnight with 10 L of PBS at pH 7.2 at 4° C.

Example 14

Development of ELISAs for Trazodone and mCPP

Trazodone and mCPP were coupled by way of a crosslinker to bovine thyroglobulin (Examples 7 and 12). The resulting immunogens were administered separately to adult sheep on a monthly basis to provide target-specific polyclonal antisera. IgG was extracted from the antisera via caprylic acid/ammonium sulphate precipitation of immunoglobulin. Microtitre plates (Thermo Scientific, 95029180) were coated with antibody (125 µl) in coating buffer (10 mM Tris pH 8.5) at 37° C. for 2 hours. Antibody raised from the mCPP-derived immunogen was coated at 2.5 µg/ml and antibody raised from the trazodone-derived immunogen was coated at 0.625 µg/ml. The plates were then washed. 50 µl of sample/standard (trazodone, Sigma T6154-1 g; mCPP, Alfa-Aesar L01772; nefazodone, Sigma N5536) was added to the appropriate wells in triplicate, followed by 75 µl of conjugate from Example 13 for the generic antibody, and 75 µl of conjugate from Example 8 for the trazodone-specific antibody) and incubated at 25° C. for 1 hour. The plates were then washed and 125 µl of TMB (Randox, 4380-15) was added to each well and left at room temperature for 20 minutes in the dark. The reaction was stopped using 125 µl of 0.2M sulphuric acid. The absorbances were then read at 450 nm with an ELISA microplate reader (BIO-TEK Instruments, EL340) and the means calculated. Antibody specificity and sensitivity were then determined.

Results

Competitive ELISA results in Tables 1 & 2 highlight a mCPP generic antibody and a trazodone-specific antibody, respectively. An assay that makes use of both these antibodies can confirm mCPP abuse by verifying the presence of mCPP and the absence of trazodone.

TABLE 1

Generic antibody cross-reactivity and sensitivity profile

| Standard conc" ng/ml | Trazodone | | mCPP | | Nefazodone | |
| --- | --- | --- | --- | --- | --- | --- |
| | $A_{450}$ | % $B/B_0$ | $A_{450}$ | % $B/B_0$ | $A_{450}$ | % $B/B_0$ |
| 0.000 | 2.184 | 100 | 2.133 | 100 | 2.023 | 100 |
| 0.156 | 1.456 | 67 | 1.821 | 85 | 1.850 | 91 |
| 0.313 | 1.271 | 58 | 1.679 | 79 | 1.671 | 83 |
| 0.625 | 1.041 | 48 | 1.534 | 72 | 1.467 | 73 |
| 1.250 | 0.763 | 35 | 1.380 | 65 | 1.168 | 58 |
| 2.500 | 0.551 | 25 | 1.183 | 55 | 0.923 | 46 |
| 5.000 | 0.398 | 18 | 1.027 | 48 | 0.683 | 34 |
| 10.000 | 0.287 | 13 | 0.888 | 42 | 0.494 | 24 |
| $IC_{50}$ | 0.532 | | 8.476 | | 3.901 | |
| % CR | 733 | | 46 | | 100 | |

$A_{450}$ = absorbance at 450 nm;
B = absorbance at 450 nm at x ng/ml standard concentration
$B_0$ = absorbance at 450 nm at 0 ng/ml standard concentration;
$IC_{50}$ = standard concentration which produces 50% $B/B_0$;
% CR = percentage cross-reactivity based on Nefazodone (100%)

TABLE 2

Trazodone antibody cross-reactivity and sensitivity profile

| Standard conc$^n$ ng/ml | Trazodone | | mCPP | | Nefazodone | |
|---|---|---|---|---|---|---|
| | $A_{450}$ | % $B/B_0$ | $A_{450}$ | % $B/B_0$ | $A_{450}$ | % $B/B_0$ |
| 0.000 | 1.744 | 100 | 1.759 | 100 | 1.674 | 100 |
| 0.156 | 0.816 | 47 | 1.721 | 98 | 1.631 | 97 |
| 0.313 | 0.570 | 33 | 1.755 | 100 | 1.656 | 99 |
| 0.625 | 0.375 | 21 | 1.756 | 100 | 1.621 | 97 |
| 1.250 | 0.237 | 14 | 1.759 | 100 | 1.677 | 100 |
| 2.500 | 0.151 | 9 | 1.782 | 101 | 1.663 | 99 |
| 5.000 | 0.093 | 5 | 1.814 | 103 | 1.765 | 105 |
| 10.000 | 0.057 | 3 | 1.857 | 106 | 1.799 | 107 |
| $IC_{50}$ | 0.872 | | — | | — | |
| % CR | 100 | | 0.68 | | 1.38 | |

$A_{450}$ = absorbance at 450 nm;
B = absorbance at 450 nm at x ng/ml standard concentration
$B_0$ = absorbance at 450 nm at 0 ng/ml standard concentration;
$IC_{50}$ = standard concentration which produces 50% $B/B_0$;
% CR = percentage cross-reactivity based on Trazodone (100%)

BIBLIOGRAPHY

Staack R. F. et al. (2007). *J. Chromatog. B*, 855: 127-133.
Mayol R. F. et al (1994). *Drug Metab. Dispos.*, 22: 304-311.

What is claimed is:

1. A composition comprising at least one first antibody specific for at least one drug that produces m-chlorophenylpiperazine (mCPP) as a metabolic product together with a second antibody that binds mCPP.

2. The composition of claim 1, wherein the at least one drug that produces mCPP as a metabolic product is selected from the group consisting of trazodone, nefazodone and a combination thereof.

3. A kit for detecting or determining mCPP intake, the kit comprising:
   at least one antibody specific for at least one drug that produces mCPP as a metabolic product; and
   an antibody that binds an epitope of mCPP.

4. The kit of claim 3 in which the drug that produces mCPP as a metabolic product is selected from the group consisting of trazodone, nefazodone and a combination thereof.

5. The kit of claim 3, further comprising a conjugate, said conjugate comprising an enzyme and 6-[N'-(3-chlorophenyl)-N-piperazinyl]hexanoic acid.

6. The kit of claim 5, wherein the enzyme is a peroxidase.

7. The kit of claim 6, wherein the peroxidase is horseradish peroxidase (HRP).

8. The kit of claim 3, further comprising a conjugate, said conjugate comprising an enzyme and 3-(carboxymethoxy) trazodone.

9. The kit of claim 8, wherein the enzyme is a peroxidase.

10. The kit of claim 9, wherein the peroxidase is horseradish peroxidase (HRP).

11. The kit of claim 3, further comprising:
    a conjugate comprising a first enzyme and 6-[N'-(3-chlorophenyl)-N-piperazinyl]hexanoic acid; and
    a conjugate comprising a second enzyme and 3-(carboxymethoxy)trazodone.

12. The kit of claim 11, wherein the first enzyme and the second enzyme are each horseradish peroxidase (HRP).

13. A conjugate comprising:
    a labelling agent selected from the group consisting of an enzyme, a luminescent substance, a radioactive substance and a combination thereof; and
    a hapten selected from the group consisting of 6-[N'-(3-chlorophenyl)-N-piperazinyl]hexanoic acid and 3-(carboxymethoxy)trazodone.

14. The conjugate of claim 13, wherein the labelling agent is a peroxidase.

15. The conjugate of claim 14, wherein the peroxidase is horseradish peroxidase (HRP).

16. The conjugate of claim 13, wherein the hapten is 6-[N'-(3-chlorophenyl)-N-piperazinyl]hexanoic acid.

* * * * *